(12) United States Patent
Cottens et al.

(10) Patent No.: US 6,200,985 B1
(45) Date of Patent: Mar. 13, 2001

(54) RAPAMYCIN DERIVATIVES

(75) Inventors: Sylvain Cottens, Witterswil; Richard Sedrani, Basel, both of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/356,587

(22) Filed: Jul. 19, 1999

Related U.S. Application Data

(63) Continuation of application No. 08/973,604, filed as application No. PCT/EP96/02441 on Jun. 5, 1996, now Pat. No. 5,985,890.

(30) Foreign Application Priority Data

Jun. 9, 1995 (GB) ................................. 9511704
Aug. 6, 1995 (GB) ................................. 9513754

(51) Int. Cl.⁷ .................... A61K 31/695; A61P 43/00
(52) U.S. Cl. ........................................ 514/291
(58) Field of Search ............................. 514/291

(56) References Cited

U.S. PATENT DOCUMENTS

| | | | |
|---|---|---|---|
| 5,100,883 | 3/1992 | Schiehser | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 540/452 |
| 5,151,413 | 9/1992 | Caufield et al. | 514/183 |
| 5,221,670 | 6/1993 | Caufield | 514/183 |
| 5,256,790 | 10/1993 | Nelson | 514/291 |
| 5,258,389 | 11/1993 | Goulet et al. | 514/291 |
| 5,262,423 | 11/1993 | Kao | 514/291 |
| 5,310,901 | 5/1994 | Parsons et al. | 540/456 |
| 5,310,903 | 5/1994 | Goulet et al. | 540/456 |
| 5,387,680 | 2/1995 | Nelson | 540/456 |
| 5,527,907 | 6/1996 | Or et al. | 540/456 |
| 5,728,710 | 3/1998 | Luengo | 514/291 |
| 5,912,253 | 6/1999 | Cottens et al. | 514/291 |

FOREIGN PATENT DOCUMENTS

| | | |
|---|---|---|
| 551182 | 7/1993 | (EP) . |
| 568310 | 11/1993 | (EP) . |
| 691130 | 1/1996 | (EP) . |
| WO 92/05179 | 4/1992 | (WO) . |
| WO 94/02136 | 2/1994 | (WO) . |
| WO 94/04540 | 3/1994 | (WO) . |
| WO 94/09010 | 4/1994 | (WO) . |
| WO 95/14023 | 5/1995 | (WO) . |

OTHER PUBLICATIONS

Luengo et al., Tetrahedron Letters, vol. 35, No. 35, pp. 6469–6472 (1994).
Fellstrom et al., Immunological Reviews, No. 134, 83–98 (1993).
Meiser et al., Lancet, vol. 338, pp. 1297–1298 (1991).
Gregory et al., J. Heart Lung Transpl. vol. 11, pt. 11, p. 197 (1992).
Morris et al., Transplantation Proceedings, vol. 23, No. 2, Suppl 2 (Apr.), pp. 19–25 (1991).

*Primary Examiner*—Bruck Kifle
(74) *Attorney, Agent, or Firm*—Gabriel Lopez

(57) ABSTRACT

Rapamycin derivatives are disclosed of the formula:

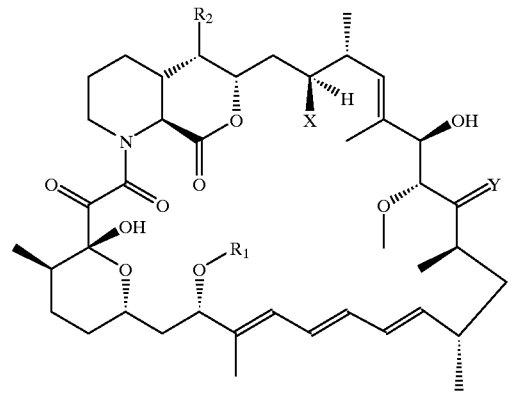

wherein the variables are in the specification.

18 Claims, No Drawings

RAPAMYCIN DERIVATIVES

This is a continuation of Ser. No. 08/973,604, Dec. 8, 1997, now U.S. Pat. No. 5,985,890, which is a 371 of PCT/EP96/02441, Jun. 5, 1996.

The present invention relates to rapamycin derivatives, a process for their production, their use as a pharmaceutical and pharmaceutical compositions containing them.

Rapamycin is a known macrolide antibiotic produced by *Streptomyces hygroscopicus*, having the structure depicted in Formula A:

(A)

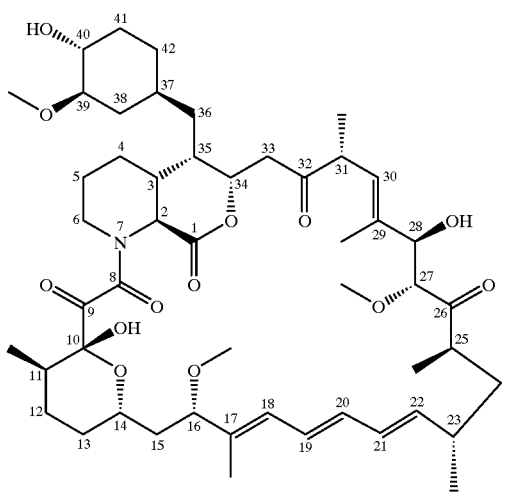

See, e.g., McAlpine, J. B., et al., *J. Antibiotics* (1991) 44: 688; Schreiber, S. L., et al., J. Am. Chem. Soc. (1991) 113: 7433; U.S. Pat. No. 3,929,992. (There have been various numbering schemes proposed for rapamycin. To avoid confusion, when specific rapamycin derivatives are named herein, the names are given with reference to rapamycin using the numbering scheme of formula A.) Rapamycin is a potent immunosuppressant and has also been shown to have antitumor and antifungal activity. Its utility as a pharmaceutical, however, is restricted by its very low and variable bioavailability. Moreover, rapamycin is insoluble and lacks stability, making it difficult to formulate stable galenic compositions.

Numerous derivatives of rapamycin are known. Certain 40-O-substituted rapamycins are described in, e.g., in U.S. Pat. No. 5,258,389 and WO 94/09010 (O-alkyl rapamycins); WO 92/05179 (carboxylic acid esters), U.S. Pat. No. 5,118,677 (amide esters), U.S. Pat. No. 5,118,678 (carbamates), U.S. Pat. No. 5,100,883 (fluorinated esters), U.S. Pat. No. 5,151,413 (acetals), and U.S. Pat. No. 5,120,842 (silyl ethers).

It has now surprisingly been discovered that certain novel derivatives of rapamycin have an improved pharmacologic profile over rapamycin, and exhibit greater stability.

According to the invention, there is provided a compound of Formula I

I

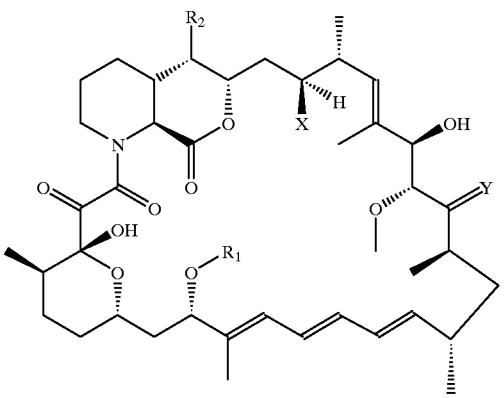

wherein
$R_1$ is alkyl, alkenyl, alkynyl, hydroxyalkyl, hydroxyalkenyl, hydroxyalkynyl, benzyl, alkoxybenzyl or chlorobenzyl,
$R_2$ is selected from formula II or formula III:

Formula II

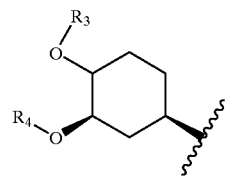

Formula III

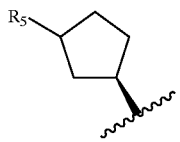

wherein
$R_3$ is selected from H, alkyl, alkenyl, alkynyl, aryl, thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl and alkylsilyl;
$R_4$ is H, methyl or together with $R_3$ forms $C_{2-6}$alkylene;
$R_5$ is $R_6O$—$CH_2$—, wherein $R_6$ is selected from H, alkyl, alkenyl, alkynyl, aryl, alkylcarbonyl, arylcarbonyl, heteroarylcarbonyl, hydroxyalkylcarbonyl, aminoalkylcarbonyl, formyl, thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl and carbalkoxyalkyl;
$R_7CO$—, wherein $R_7$ is selected from H, alkyl, hydroxy, alkoxy, aryloxy, amino, alkylamino, a residue of an amino acid, or N,N-disubstituted-amino wherein the substituents (a) are selected from alkyl, aryl or arylalkyl or (b) form a heterocyclic structure; $R_8NCH$—, wherein $R_8$ is alkyl, aryl, amino, alkylamino, arylamino, hydroxy, alkoxy or arylsulfonylamino; —O—CH—O—; or substituted dioxymethylyne;

Y is selected from O, (H, OH), and (H, $OR_9$) wherein $R_9$ is selected from $C_{1-4}$alkyl, alkylcarbonyl, arylcarbonyl, heteroarylcarbonyl, hydroxyalkylcarbonyl, aminoalkylcarbonyl, formyl or aryl; and X is OH or H;

wherein "alk" or "alkyl" refers to a $C_{1-10}$aliphatic substituent optionally interrupted by an oxy linkage; and "ar" or "aryl" refers to a monocyclic, optionally heterocyclic, optionally substituted, $C_{4-14}$aromatic substituent, provided that, when X is OH, $R_1$ is alkyl and $R_2$ is a residue of formula II, then $R_3$ is other than H.

Any "alk" moiety or "alkyl" mentioned above may be branched, linear or cyclic; preferably it is a $C_{1-6}$aliphatic substituent optionally interrupted by an oxy linkage, more preferably uninterrupted by oxy.

Examples of "ar" moiety or "aryl" mentioned above and optionally substituted may include e.g. phenyl, benzyl, tolyl, pyridyl and the like.

When $R_1$ is chlorobenzyl or alkoxybenzyl, the substituent is preferably in ortho.

When $R_7CO$— is N,N-disubstituted-carbamoyl, it may be e.g. N-methyl-N-(2-pyridin-2-yl-ethyl)-carbamoyl, (4-methyl-piperazin-1-yl)-carbonyl or (morpholinyl) carbonyl.

When $R_5$ is substituted dioxymethylyne, it may be e.g. O,O-(alkylene)-dioxy-methylyne, i.e. wherein the 2 oxygens are linked by an alkylene group.

In the compounds of formula I, the following significances are preferred either individually or in any combination or sub-combination:

1. X is OH and $R_1$ is $C_{3-10}$alkynyl or $C_{3-10}$hydroxyalkynyl, preferably $C_{3-10}$-alk-2-ynyl or $C_{3-10}$hydroxyalk-2-ynyl, more preferably $C_{3-6}$alk-2-ynyl;
2. X is H and $R_1$ is $C_{1-10}$alkyl, $C_{3-10}$alk-2-enyl, $C_{3-10}$hydroxyalk-2-enyl, $C_{3-10}$alk-2-ynyl, $C_{3-10}$hydroxyalk-2-ynyl or $C_{1-10}$alkoxy$C_{1-10}$alkyl, preferably $C_{1-6}$alkyl or $C_{3-6}$alk-2-ynyl, more preferably $C_{1-4}$alkyl, most preferably methyl;
3. $C_{3-6}$alkynyl as $R_1$ is 2-propynyl or pent-2-ynyl, preferably pent-2-ynyl;
4. Y is O, (H, OH) or (H, $C_{1-4}$alkoxy), preferably O;
5. $R_2$ is a residue of formula II;
6. In the residue of formula II, $R_3$ is H, $C_{1-6}$hydroxyalkyl, hydroxy-$C_{1-6}$alkoxy-$C_{1-6}$alkyl, ($C_{1-6}$alkyl)-carbonyl-amino-$C_{1-6}$-alkyl, $C_{1-6}$alkoxy-$C_{1-6}$alkoxy or amino-$C_{1-6}$alkyl, preferably H, hydroxyethyl, hydroxypropyl, hydroxyethoxyethyl, methoxyethyl or acetylaminoethyl; especially H when X is H or when X is OH and $R_1$ is alkynyl;
7. In the residue of formula II, $R_4$ is methyl.
8. $R_2$ is a residue of formula III wherein $R_5$ is $R_6OCH_2$— wherein $R_6$ is selected from H, $C_{1-6}$alkyl, $C_{3-6}$alk-2-enyl, $C_{3-6}$alk-2-ynyl, aryl; $C_{1-6}$alkyl-carbonyl, arylcarbonyl, hydroxy$C_{1-6}$alkyl, $C_{1-6}$alkoxy-$C_{1-6}$alkyl or amino$C_{1-6}$alkyl; $R_7CO$— wherein $R_7$ is selected from H, hydroxy, $C_{1-6}$alkoxy, amino, $C_{1-6}$alkylamino, a residue of an amino acid or N,N-disubstituted amino wherein the substituents (a) are selected from $C_{1-6}$alkyl or aryl or (b) form a heterocyclic structure; $R_8NCH$— wherein $R_8$ is alkyl, aryl, amino, alkylamino, arylamino, hydroxy, alkoxy or arylsulfonylamino; —O—CH—O—; or substituted dioxymethylyne.

Preferred compounds are compounds of formula Ia

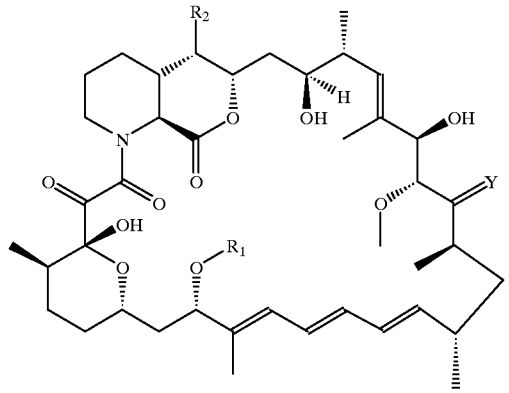

Ia wherein $R_1$, $R_2$ and Y are as defined above, preferably have any of the preferred significances given under 1. and 3. to 8. above;

and of formula Ib

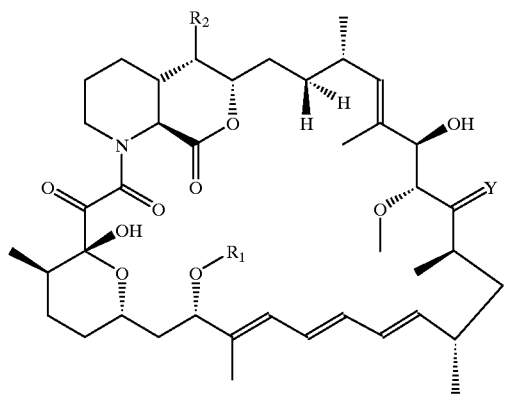

Ib wherein $R_1$, $R_2$ and Y are as defined above, preferably have any of the preferred significances given under 2. to 8. above.

Especially preferred compounds include (i) 32-deoxo-rapamycin;
(ii) 16-O-pent-2-ynyl-32deoxo-rapamycin;
(iii) 16-O-pent-2-ynyl-32-deoxo40-O-(2-hydroxy-ethyl) rapamycin
(iv) 16-O-pent-2-ynyl-32(S)-dihydro-rapamycin;
(v) 16-O-pent-2-ynyl-32(S)-dihydro-40-O-(2-hydroxyethyl)-rapamycin;
(vi) 32(S)-dihydro-40-O-(2-methoxyethyl-rapamycin;
(vii) 32(S)-dihydro-40O-(2-hydroxyethyl)rapamycin.

Compounds of formula I may exhibit isomerism and accordingly further isomeric forms will exist. It will be understood that the present invention embraces compounds of formula I, the individual isomers of formula I'

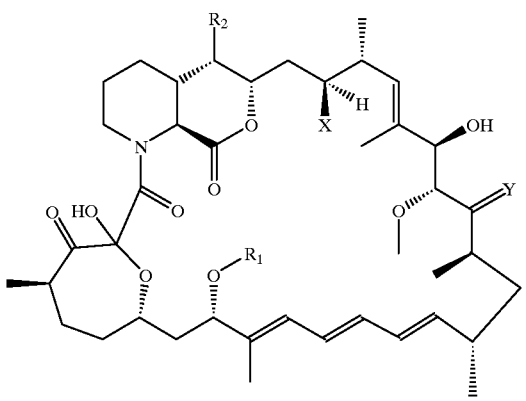

I' wherein $R_1$, $R_2$, Y and X are as defined above, as well as isomeric mixtures thereof.

The individual isomers may be separated by analogy to methods known in the art.

The present invention also provides a process for the production of the compounds of formula I which process comprises a) to produce a compound of formula I wherein X is H, reductively eliminating the carbonyl in position 32 of a compound of formula IVa

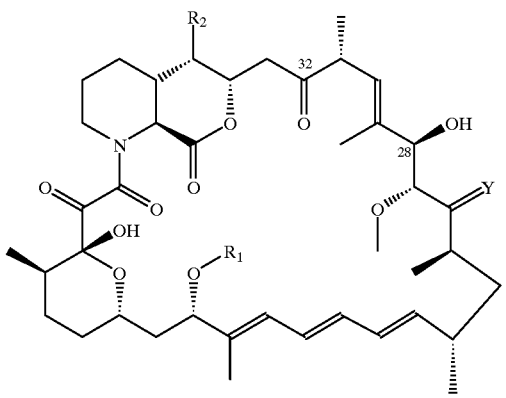

IVa wherein $R_1$, $R_2$ and Y are as defined above, in protected or unprotected form,
and, where required, removing the protecting groups present; or b) to produce a compound of formula I wherein X is OH, stereoselectively reducing the carbonyl in position 32 of a compound of formula IVa as defined above; or c) converting a compound of formula I wherein $R_1$ is alkyl to provide a compound of formula I wherein $R_1$ is other than alkyl.

In process step a), the compound of formula IVa is preferably in protected form, i.e. it may comprise protecting groups on functional groups which do not participate in the reaction, e.g. OH in position 28 and optionally in position 40 when $R_2$ is a residue of formula II or in position 39 when $R_2$ is a residue of formula III.

The reduction a) to the 32-deoxo compound of formula I may conveniently be performed in two steps:

i) by reacting a compound of formula IVa preferably in protected form with a hydride, e.g. diisobutyl aluminium hydride or preferably lithium tri-tert-butoxyaluminium hydride, to produce a corresponding 32-dihydro compound. Other methods and reagents as known in the art for reducing ketones may be used for producing the 32-dihydro compound from the corresponding ketone. They include e.g. hydrogenation, reduction by metals, metal hydride reduction, as described in Comprehensive Organic Transformations, R. C. Larock, VCH Publishers Inc., New York, 1989, pp. 527–535, sections 7.1.1–7.1.4 and asymmetric reduction methods for ketones, e.g. as disclosed in Comprehensive Organic Transformations, R. C. Larock, VCH Publishers Inc., New York, 1989, pp. 540–547, section 7.1.15. The reduction step i) is then followed ii) by converting the 32-dihydro compound into the corresponding 32-halo-derivative, e.g. 32-bromo- or (preferably) 32-iodo-derivative, which is then reduced e.g. by a hydride into the desired 32-deoxo derivative and where required deprotecting the resulting compound Further reagents such as used for reducing halides may be used and include e.g. low valent metals (i.e. lithium, sodium, magnesium and zinc) and metal hydrides (aluminium hydrides, borohydrides, silanes, copper hydrides) (see Comprehensive Organic Transformations, R. C. Larock, VCH Publishers Inc., New York, 1989, pp. 18–20, sections 1.5.1. and 1.5.2.).

Alternatively, halide reduction can be achieved by use of hydrogen or a hydrogen source (i.e. formic acid or a salt thereof) in the presence of a suitable metal catalyst (i.e. Raney-nickel, palladium metal or palladium complexes, complexes of rhodium or ruthenium) (see Comprehensive Organic Transformations, R. C. Larock, VCH Publishers Inc., New York, 1989, pp. 2024, section 1.5.3.). Furthermore, known methods as used for transforming an alcohol into the corresponding deoxy compound, may also be employed. These methods include e.g. direct reduction or reduction of an intermediate phosphorous compound, sulfonate, thiocarbonate, thiocarbamate or xanthate and are described e.g. in Comprehensive Organic Transformations, R. C. Larock, VCH Publishers Inc., New York, 1989, pp. 27–31, sections 1.9.1.–1.9.4.

Suitable hydroxy protecting groups and methods for their formation and removal are known in the art, e.g. see Protective-Groups in Organic Synthesis, second ed. T. W. Greene and P. G. M. Wuts, John Wiley & Sons, New York, 1991, Chapter 2 and references therein. Preferred OH protecting groups are e.g. triorganosilyl groups such as tri($C_{1-6}$)alkylsilyl (e.g. trimethylsilyl, triethylsilyl), triisopropylsilyl, isopropyldimethylsilyl, t-butyldimethylsilyl, triarylsilyl (e.g. triphenylsilyl) or triaralkylsilyl (e.g. tribenzylsilyl). Deprotection may be carried out under mildly acidic conditions.

The reduction step i) may conveniently be effected at a low temperature, e.g. from −10 to −80° C.

In step ii) the 32-dihydro compound optionally in protected form, preferably the 32(R)diastereoisomer, is converted into an ester, preferably a sulphonate, e.g. mesylate, tosylate, nosylate or triflate, followed by displacement with a suitable halide, e.g. sodium iodide or bromide, tetrabutyl ammonium iodide or bromide, preferably in the presence of a base, e.g. an amine. The 32(R)diastereoisomer may be separated from the mixture according to known separation techniques e.g. chromatography.

Suitable hydrides to reduce the 32-halo compound include e.g. radical hydrides such as tributyltin hydride or tris-(trimethylsilyl)silane. Reduction may also be performed in the absence or presence of a radical initiator, e.g. 2,2'- azobisisobutyronitrile or preferably Et₃B, conveniently at a temperature from 0° to 80° C.

An oxidant such as cupric acetate may be conveniently added after the reduction step of i) or ii), if required, to re-oxidize selectively into carbonyl an undesired side reduction which may occur e.g. in position 9.

Alternatively, the 32-dihydro derivative may be directly converted into a halide by methods known in the art, e.g. using triphenylphosphine in combination with N-bromo or N-iodo-succinimide, carbontetrabromide or tetraiodide, 1,2-dibromotetrachloroethane, 2,4,5-tribromo- or -triiodoimidazole, iodine, 1,2-diodoethane, or using thionyl bromide or methyltriphenoxy phosphonium iodide.

The reduction of the carbonyl in position 32 into the 32-deoxo derivative may also be performed through the formation of a tosylhydrazone followed by treatment with a borane, e.g. catecholborane, or through the formation of a dithiane followed by suitable reduction, e.g. with Raney Nickel or a hydride, e.g. tributyltin hydride. Other known methods for transforming a ketone into the corresponding alcane may be used; such methods include e.g. direct reduction (see Comprehensive Organic Transformations, R. C. Larock, VCH Publishers Inc., New York, 1989, pp. 35–37, section 1.12.1.) or reduction via hydrazones (Comprehensive Organic Transformations, R. C. Larock, VCH Publishers Inc., New York, 1989, pp. 37–38, section 1.12.2.) and via sulfur and selenium derivatives (Comprehensive Organic Transformations, R. C. Larock, VCH Publishers Inc., New York, 1989, pp. 34–35, sections 1.10. and 1.11.).

The reduction step b) to the 32(S)dihydro compound of formula I is performed under selected conditions. Preferably a reducing agent which significantly favours the reduction to 32(S), e.g. sodium triethylborohydride, is used. The reduction may conveniently be carried out at a low temperature, e.g. from −50 to −80° C., in an inert solvent, e.g. THF diethylether, glyme, diglyme or methyl t.-butyl ether. The separation of the 32(S)-dihydro compound from the low amounts of the 32(R)-dihydo compound produced may be performed by methods known in the art, e.g. column chromatography, reverse phase chromatography.

If desired, the hydroxy groups in position 28 and optionally in position 40 may be protected prior to the reduction and deprotected afterwards, e.g. as disclosed above. Preferably the reduction step b) is performed without OH-protection.

The conversion step c) may be carried out according to methods known in the art. For example, a compound of formula I wherein R, is alkyl, preferably methyl, may be reacted with a compound $R_x$—OH wherein R is alkynyl or hydroxyalkynyl to provide a compound of formula I wherein R, is alkynyl or hydroxyalkynyl. The reaction may conveniently be carried out in an aprotic solvent, e.g. dichloromethane, toluene, acetonitrile or THF under acidic conditions.

Preferably the reduction in position 32, particularly the reduction step b) is carried out on a compound of formula IVa wherein $R_1$ has already the desired significance, e.g. $R_1$ is alkynyl, thus avoiding a later conversion after reduction. A compound of formula IVa wherein $R_1$ is alkynyl or hydroxyalkynyl, used as starting material, may be prepared using a compound $R_x$—OH as disclosed above.

Compounds used as starting materials may be prepared analogously to methods known and practiced in the art, e.g. as disclosed in U.S. Pat. No. 5,258,389, WO 94/09010, WO 95/16691, U.S. Pat. No. 5,120,842 etc.

The following examples are illustrative of the invention. All temperatures are in ° C. The following abbreviations are used:

THF=tetrahydrofuran
TES=triethyl silyl

EXAMPLE 1

32-Deoxorapamycin ($R_1$=CH₃; $R_2$=II wherein $R_3$=H and $R_4$=CH₃; X=H; Y=O)

To a stirred, cooled (−78°) solution of 26.1 g (22.85 mmol) of 28,40-bis—O-TES-rapamycin in 260 ml of TBF is added 50.3 ml (50.3 mmol) of a 1M solution of lithium-tri-t.-butoxyaluminum hydride in TBF. The resulting mixture is allowed to warm to −15° over 2 hours. Then the cooling bath is replaced by an ice bath, bringing the temperature to 0°, and stirring is continued for 1 hour at this temperature. The reaction mixture is poured into a separating funnel containing 750 ml of ethyl acetate and 400 ml of ice-cold 2N aqueous citric acid and briefly shaken. The aqueous layer is separated and extracted twice with cold ethyl acetate. The combined organic solution is washed with ice-cold 2N aqueous citric acid, water, saturated aqueous sodium bicarbonate and twice with saturated brine, then dried over anhydrous sodium carbonate, filtered and concentrated under reduced pressure. The residue, consisting of a mixture of 32(R)-dihydro-28,40-bis-O-TES-rapamycin and (32R) 9,32-bis-dihydro-28,40-bis-O-TES-rapamycin, is dissolved without further purification in 260 ml of methanol. This solution is cooled to 0° and treated with 6.85 g (34.31 mmol) of cupric acetate. After stirring for I hour, the resulting suspension is diluted with methyl-t.-butyl ether and washed twice with water and twice with saturated brine. The aqueous layers are backextracted with methyl-t-butyl ether. The combined organic solution is dried over anhydrous sodium sulfate, filtered and concentrated under reduced pressure. The residue is purified by silica gel chromatography (60:40 hexane/methyl-t-butyl ether) to afford pure 32(R)-dihydro-28,40-bis-O-TES-rapamycin as a white solid.

¹H NMR (CDCl₃) 4:1 mixture of rotamers, chemical shifts in parentheses refer to the minor rotamer δ 0.72 (1H, dd, H-38ax), 1.63 (1.60) (3H, s, C17-CH₃), 1.66 (1.69) (3H, s, C29-CH₃), 1.77 and 1.81 (H-33), 2.46 (1H, m, H-31), 2.82 (2.91) (1H, m, H-25), 2.91 (1H, m, H-39), 3.13 (3H, s, C16-OCH₃), 3.26 (3H, s, C27-OCH₃), 3.41 (1H, m, H-40), 3.43 (3H, s, C39-OCH₃), 3.62 (1H, m, H-32), 3.75 (3.57) (1H, d, H-27), 4.10 (1H, d, H-28), 4.81 (1H, broad s, C10—OH), 5.05 (1H, d, H-34), 5.27 (1H, d, H-30), 5.36 (1H, d, H-2), 5.69 (1H, dd, H-22), 6.03 (5.96) (1H, d, H-18), 6.15 (1H, dd, H-21), 6.33 (1H, dd, H-20), 6.40 (1H, dd, H-19)

MS (FAB, LiI matrix) m/z 1150 ({M+Li}⁺) (rel. intensity 100)

To a stirred, cooled (−15°) solution of 20.69 g (18.10 mmol) of 32(R)-dihydro-28,40-bis-O-TES-rapamycin and 7.55 ml (54.27 mmol) of triethylamine in 200 ml of methylene chloride is added 2.10 ml (27.02 mmol) of methanesulfonyl chloride. The mixture is stirred for 20 minutes, then diluted with ethyl acetate and saturated aqueous sodium bicarbonate is added. The layers are separated and the aqueous layer is extracted three times with ethyl acetate. The combined organic phase is washed with saturated aqueous sodium bicarbonate and brine, dried over anhydrous sodium sulfate, filtered and concentrated under reduced pressure. The residue may be purified by column chromatography on silica gel (80:20 hexane/ethyl acetate) affording pure 32(R)-dihydro-32-O-mesyl-28,40-bis-O-TES-rapamycin as a white solid, but routinely the crude product is used in the subsequent step without further purification.

¹H NMR (CDCl₃) δ 0.77 (1H, dd, H-38ax), 1.67 (3H, s, C17-CH₃), 1.72 (3H, s, C29-CH₃), 2.77 (1H, M, H-25), 2.92 (1H, m, H-39), 3.03 (3H, s, C16-OCH₃), 3.17 (3H, s,

C27-OCH$_3$), 3.21 (3H, s, C39-OCH$_3$), 3.42 (1H, m, H-40), 3.45 (3H, s, CH$_3$SO$_3$), 3.91 (1H; d, H-27), 4.10 (1H, d, H-28), 4.72 (1H, m, H-32), 4.94 (1H, s, C10-OH), 5.12 (1H, m, H-34), 5.25 (1H, d, H-30), 5.88 (1H, d, H-2), 5.88 (1H, dd, H-22), 6.03 (1H, d, H-18), 6.18 (1H, dd, H-21), 6.37 (1H, dd, H-20), 6.44 (1H, dd, H-19)

MS (FAB, LiI matrix) m/z 1228 ([M+Li]$^+$) (rel. intensity 68), 1132 ([(M−CH$_3$SO$_3$H)+Li]$^+$) (rel. intensity 100)

A mixture of 22.35 g (18.30 mmol) of 32(R)-dihydro-32-O-mesyl-28,40-bis-O-TES-rapamycin, 27.50 g (183.33 mmol) of sodium iodide and 6.3 ml (36.68 mmol) of diisopropylethylamine in 400 ml of TBF is heated to reflux for 6 hours, then is allowed to cool to room temperature. The resulting mixture is diluted with ethyl acetate and treated with 38.4% aqueous sodium bisulfite. The layers are separated. The organic phase is washed three times with saturated aqueous sodium bicarbonate and once with saturated brine, then dried over anhydrous sodium sulfate, filtered and concentrated under reduced pressure. The residue is purified by column chromatography on silica gel (83:17 hexane/ethyl acetate) to afford pure 32(S)-deoxo-32-iodo-28,40bis-0-TES-rapamycin.

$^1$H NMR (CDCl$_3$) 1.5:1 mixture of rotamers, chemical shifts in parentheses refer to the minor rotamer δ 0.73 (1H, dd, H-38ax), 1.68 (1.66) (6H, s, C17-CH$_3$ and C29-CH$_3$), 2.72 (1H, m, H-25), 2.91 (2I, m, H-32 and H-39), 3.15 (3H, s, C16-OCH$_3$), 3.30 (3.31) (3H, s, C27-OCH$_3$), 3.43 (3.41) (3H, s, C39-OCH$_3$), 3.77 (3.91) (1H, d, H-27), 4.21 (4.25) (1H, d, H-28), 4.51 (1H, s, C10-OH), 5.45 (5.48) (1H, d, H-30), 5.60 (5.79) (1H, dd, H-22), 6.02 (5.85) (1H, d, H-18)

MS (FAB, LiI matrix) m/z 1260 ([M+Li]$^+$) (rel. intensity 100)

To a stirred, cooled (0°) solution of 16.79 g (13.19 mmol) of 32(S)-deoxo-32-iodo-28,40-bis-O-TES-rapamycin in 190 ml of toluene is added 7 ml (26.38 mmol) of tributyltin hydride followed by 1.3 ml (1.30 mmol) of a 1M solution of triethylborane in hexane. This mixture is stirred for 30 minutes and quenched with saturated aqueous ammonium chloride. The layers are separated and the aqueous layer is extracted twice with ethyl acetate. The combined organic layers are washed with water, saturated aqueous sodium bicarbonate, water and three times with saturated brine, then dried over anhydrous sodium sulfate, filtered and concentrated under reduced pressure. The residue is purified by column chromatography on silica gel (75:25 hexane/methyl-t-butyl ether) to afford pure 32-deoxo-28,40-bis-O-TES-rapamycin as a white solid.

$^1$H NMR (CDCl$_3$) 2.5:1 mixture of rotamers, chemical shifts in parentheses refer to the minor rotamer δ 0.73 (1H, dd, H-38ax), 1.62 (1.57) (3H, s, C17-CH$_3$), 1.68 (1.72) (3H, s, C29-CH$_3$), 2.77 (2.91) (1H, m, H-25), 2.91 (1H, m, H-39), 3.15 (3H, s, C16-OCH$_3$), 3.27 (3.25) (3H, s, C27-OCH$_3$), 3.43 (3.45) (3H, s, C39-OCH$_{3, 3.70}$ (3.67) (1H, d, H-27), 4.11 (4.07) (1H, d, H-28), 4.57 (1H, broad s, C10-OH), 4.87 (4.67) (1H, cd, H-34), 5.19 (5.08) (1H, d, H-30), 5.32 (1H, d, H-2), 5.60 (5.66) (1H, dd, H-22), 6.01 (5.92) (1H, d, H-18), 6.17 (1H, dd, H-21), 6.30 (1H, dd, H-20), 6.40(1H, dd, H-19)

MS (FAB, LiI matrix) m/z 1134 ([M+Li]$^+$) (rel. intensity 100)

To a stirred, cooled (−15°) solution of 10.73 g (9.52 mmol) of 32-deoxo-28,40-bis-O-TES-rapamycin in 85 ml of methanol is added dropwise 9.5 ml of 2N aqueous sulfuric acid. After the addition is complete, the reaction mixture is warmed to 0° and stirred for 1.5 hour, then diluted with ethyl acetate and quenched with saturated sodium bicarbonate. The layers are separated and the aqueous layer is extracted with three portions of ethyl acetate. The combined organic phase is washed three times with saturated sodium bicarbonate and with brine, then dried over anhydrous sodium sulfate, filtered and concentrated under reduced pressure. The residue is dissolved in-diethyl ether whereupon the desired 32-deoxo-rapamycin crystallizes (colorless crystals).

$^1$H NMR (CDCl$_3$) 3:1 mixture of rotamers, chemical shifts in parentheses refer to the minor rotamer δ 0.70 (1H, dd, H-38ax), 1.14 and 1.32 (H-32), 1.56 (H-33), 1.65 (1.62) (3H, s, C17-CH$_3$), 1.68 (1.70) (3H, s, C29-CH$_3$), 2.31 (2H, m, H-23 and H-31), 2.82 (2.95) (1H, m, H-25), 2.95 (1H, m, H-39), 3.14 (3H, s, C16OCH$_3$), 3.32 (3H, s, C27-OCH$_3$), 3.38 (1H, m, H-40), 3.43 (3.41) (3H, s, C39-OCH$_3$), 3.61 (1H, d, H-27), 4.12 (1H, d, H-28), 4.80 (4.71) (1H, d, H-34), 5.22 (1H, d, 1L-30), 5.31 (1H, d, H-2), 5.56 (1H, dd, H-22), 5.95 (5.87) (1H, d, H-18), 6.16 (1H, dd, H-21), 6.36 (1H, dd, H-20), 6.41 (1H, dd, H-19)

MS (FAB, LiI matrix) m/z 906 ([M+Li]$^+$) (rel. intensity 100)

EXAMPLE 2

16-pent-2-ynyloxy-32(S)-dihydro rapamycin (R$_1$=pent-2-ynyl; R$_2$=H wherein R$_3$=H and R$_4$=CH$_3$; X=OH; Y=O)

To a stirred, cooled (0°) solution of 970 mg (1.06 mmol) of 32(S)-dihydrorapamycin and 1.39 ml (15.00 mmol) of 2-pentyn-1-ol in 20 ml of methylene chloride is added 0.50 ml (6.50 mmol) of trifluoroacetic acid. The mixture is stirred at 0° for 3 hours and quenched with saturated aqueous sodium bicarbonate. The layers are separated and the aqueous layer is extracted with three portions of ethyl acetate. The combined organic solution is washed with saturated brine, dried over anhydrous sodium sulfate, filtered and concentrated under reduced pressure. The crude mixture is purified by column chromatography on silica gel (20:80 hexane-ethyl acetate), then by reverse phase HPLC (RP18, 81:19 methanol-water) to afford the title compound as a white amorphous solid $^1$H NMR (CDCl$_3$) 2.5:1 mixture of rotamers, chemical shifts in parentheses refer to the minor rotamer δ 0.71 (1H, dd, H-38 ax), 1.13 (1.05) (3H, t, CH$_3$CH$_2$CCCH$_2$O), 1.67 (3H, s, 17-CH$_3$), 1.69 (3H, s, 29-CH$_3$), 2.21 (2H, qt, CH$_3$CH$_2$CCCH$_2$O), 2.96 (1H, m, H-39), 3.33 (3.37) (3H, s, 27-OCH$_3$), 3.41 (3.39) (3H, s, 39 H$_3$), 3.78 (1H, dt, CH$_3$CH$_2$CCCHHO), 4.0 (1H, dt, CH$_3$CH$_2$CCCHHO), 5.52 (5.71) (1H, dd, H-22), 5.98 (5.83) (1H, d, H-18), 6.15 (1H, m, H-21), 6.30 (1H, dd, H-20), 6.40 (1H, dd, H-19)

MS (FAB) m/z 974 ([M+Li]$^+$)

EXAMPLE 3

16-pent-2-ynyloxy-32(S)-dihydro rapamycin (Alternative Route)

Rapamycin is reacted with 2-pentyn-1-ol in a procedure analogous to that of Example 2 to yield 16-pent-2-ynyloxy-rapamycin.

To a stirred, cooled (−77°) solution of 175 g (18.1 mmol) of 16demethoxy-16-pent-2-ynyloxy-rapamycin in 180 ml of TBF are added 21.7 ml (21.7 mmol) of a 1M solution of sodium triethylborohydride in TBF. After 1 h at −77° the reaction is quenched and neutralized with a 10% citric acid aqueous solution. The reaction mixture is then allowed to come to room temperature and most of the THF is removed by evaporation under reduced pressure. The resulting solution is extracted twice with ethyl acetate, the organic phases are combined and dried over sodium sulfate. After evaporation of the solvent the crude reaction product is chromatographed over silica gel eluting with hexane/acetone 7/3. The final purification is achieved by preparative HPLC (RP-18, 76:24 methanol:water) to afford the title compound as a white amorphous solid.

The spectral data are identical to the ones of the product obtained by the other route.

EXAMPLE 4
32(S)dihydro-400-(2-methoxy)ethyl-rapamycin ($R_1=CH_3$; $R_2=H$ wherein $R_3=$2-methoxyethyl and $R_4=CH_3$; X=OH; Y=O)

To a stirred, cooled (0°) solution of 2.17 g (2.00 mmol) of 40-O-(2-methoxy)ethyl-28-O-TES-rapamycin in 20 ml of THF is added dropwise 4.4 ml (4.4 mmol) of a 1M solution of L-Selectride® in THF. The resulting yellow solution is stirred for three hours at 0° and the excess hydride reagent is quenched by the addition of 2 ml of MeOH. The solution is diluted with methyl-t-butyl ether and saturated aqueous Rochelle's salt solution is added. This mixture is allowed to warm to room temperature and stirring is continued for 15 minutes. The layers are separated and the organic solution is washed with cold 1N HCl, saturated brine, 1N sodium bicarbonate and again with brine. The aqueous washings are back-extracted with methyl-t-butyl ether. The combined organic layers are dried over anhydrous sodium sulfate, filtered and concentrated under reduced pressure to afford a crude mixture of the 32S and 32R isomers of 32-dihydro-40-(2-methoxy)ethyl-28-O-TES-rapamycin.

The crude product obtained above is dissolved in 20 ml of acetonitrile and cooled to 00. To the resulting solution is added 2 ml of HF pyridine complex. Stirring is continued for 1 hour and 1N sodium bicarbonate is added. This mixture is extracted three times with metyl-t-butyl ether. The combined organic solution is washed with 1N sodium bicarbonate and saturated brine, dried over anhydrous sodium sulfate, filtered and concentrated under reduced pressure. Purification is carried out by reverse phase HPLC (RP 18, 5 $\mu$m, 50:50–100:0 acetonitrile-water over 60 minutes) affording 32(S)-dihydro40-O-(2-methoxy)ethyl rapamycin and 32(R)-dihydro-40-O-(2-methoxy)ethyl-rapamycin as by-product.

32(S)-dihydro40-O-(2-methoxy)ethyl-rapamycin: $^1$H NMR ($CDCl_3$) 2:1 mixture of rotamers, chemical shifts in parentheses refer to the minor rotamer δ 0.77 (1H, dd, H-38 ax), 1.67 (6H, s, $C17-CH_3$ and $C29-CH_3$), 2.50 (1H, m, H-31), 3.01 (1H, m, H-25), 3.12 (2H, m, H-39 and $H_{40}$), 3.14 (3.15) (3H, s, $OCH_3$), 3.28 (1H, m, H-32), 3.36 (3.34) (3H, s, $OCH_3$), 3.39 (3.38) (3H, s, $OCH_3$), 3.48 (3.46) (3H, s, $OCH_3$), 3.55 and 3.75 (4H, 2m, $OCH_2CH_2O$), 3.84 (1H, n, H-14), 4.12 (4.16) (1H, d, H-28), 4.73 (1H, s, C10-OH), 5.03 (1H, m, H-34)
MS (FAB) m/z 980 ([M+Li]$^+$)

EXAMPLE 5
(32S)-dihydro40-(2-hydroxy)ethyl-rapamycin ($R=CH_3$; $R_2=H$ wherein $R_3=$—$CH_2CH_2OH$ and $R_4=CH_3$; X=OH; Y=O)

By following the procedure of Example 4, but using the appropriate starting material, the title compound is obtained.

(32S)dihydro40-O-(2-hydroxy)ethyl-rapamycin: $^1$H NMR ($CDCl_3$) 1.7:1 mixture of rotamers, chemical shifts in parentheses refer to the minor rotamer δ 0.76 (1H, dd, H-38ax), 2.50 (1H, m, H-31), 3.10 (1H, m, H-39), 3.13 (3.14) (3H, s, $C16-OCH_3$), 3.20 (1H, m, H-40), 3.28 (1H, m, H-32), 3.36 (3.38) (3H, s, $C27-OCH_3$), 3A5 (3A3) (3.41) (3H, s, $C39-OCH_3$), 3.50 (1H, d, H-27), 3.58 and 3.70 (4H, m, $OCH_2CH_2OH$), 4.12 (4.16) (1H, d, H-28), 5.06 (1H, m, H-34), 5.60 (1H, dd, H-22), 5.99 (1H, d, H-18), 6.17 (1H, dd, H-21), 6.33 (1H, dd, H-20), 6.42 (1H, dd, H-19)
MS (FAB, LiI matrix) m/z 966 ([M+Li]$^+$) (rel. intensity 100)

EXAMPLE 6
16-pent-2-ynyloxy-32-deoxo rapamycin ($R_1=$pent-2-ynyl; $R_2=H$ wherein $R_3=H$ and $R_4=CH_3$; X=H; Y=O)

By following the procedure of Examples 1 and 2 or 3, but using the appropriate starting materials, the title compound is obtained.

$^1$H NMR ($CDCl_3$) δ 0.70 (1H, dd, H-38ax), 1.23 (3H, t, $CH_3CH_2CCCH_2O$), 2.21 (2H, ddq, $CH_3CH_2CCCH_2O$), 2.78 (1H, m, H-25), 2.94 (1H, n, H-39), 3.31 (3H, s, $C27-OCH_3$), 3.42 (3H, s, $C39-OCH_3$), 3.62 (1H, d, H-27), 3.78 (1H, ddd, $CH_3CH_2CCCH_2O$), 4.02 (1H, ddd, $CH_3CH_2CCCH_2O$), 4.12 (1H, d, H-28), 4.79 (1H, m, H-34), 5.20,(1H, d, H-30), 5.28 (1H, broad d, H-2), 5.50 (1H, dd, H-22), 5.97 (1H, d, H-18), 6.14 (1H, dd, H-21), 6.30 (1H, dd, H-20), 6.38 (1H, dd, H-19)
MS (FAB, LiI matrix) m/z 958 ([M+Li]$^+$) (rel. intensity 100)

The Compounds of formula I exhibit pharmaceutical activity and are, therefore, useful as pharmaceuticals.

In particular the compounds of formula I have immunosuppressive and antiproliferative activity as indicated in the following in vitro and in vivo test methods:

1. Mixed lymphocyte reaction (MLR)

The Mixed Lymphocyte Reaction was originally developed in connection with allografts, to assess the tissue compatibility between potential organ donors and recipients, and is one of the best established models of immune reaction in vitro. A murine model MLR, e.g., as described by T. Meo in "Immunological Methods", L. Lefkovits and B. Pernis, Eds., Academic Press, N.Y. pp. 227–239 (1979), is used to demonstrate the immunosuppressive effect of the Compounds of formula I. Spleen cells ($2\times10^5$/well) from Balb/c mice (female, 8–10 weeks) are co-incubated on microtiter plates for 5 days with $0.5\times10^6$ irradiated (2000 rads) or mitomycin C treated spleen cells from CBA mice (female, 8–10 weeks). The irradiated allogeneic cells induce a proliferative response in the Balb/c spleen cells which can be measured by labeled precursor incorporation into the DNA. Since the stimulator cells are irradiated (or mitomycin C treated) they do not respond to the Balb/c cells with proliferation but do retain their antigenicity. The antiproliferative effect of the Compounds of formula I on the Balb/c cells is measured at various dilutions and the concentration resulting in 50% inhibition of cell proliferation ($IC_{50}$) is calculated. The inhibitory capacity of the test sample may be compared to rapamycin and expressed as a relative $IC_{50}$ (i.e. $IC_{50}$ test sample/$IC_{50}$ rapamycin). The compounds of Examples 1 and 2 have been found to have in this test a relative $IC_{50}$ of 0.3 and 0.08, respectively.

2. IL-6 mediated proliferation (IL-6 PROL)

The capacity of the Compounds of formula I to interfere with growth factor, associated signalling pathways is assessed using an interleukin-6 (IL-6)-dependent mouse hybridoma cell line. The assay is performed in 96-well microtiter plates. 5000 cells/well are cultivated in serum-free medium (as described by M. H. Schreier and R. Tees in Immunological Methods, I. Lefkovits and B. Pernis, Eds., Academic Press 1981, Vol. 1, pp. 263–275), supplemented with 1 ng recombinant IL-6/ml. Following a 66 hour incubation in the absence or presence of a test sample, cells are pulsed with 1 $\mu$Ci (3-H)thymidine/well for another 6 hours, harvested and counted by liquid scintillation. (3-H)thymidine incorporation into DNA correlates with the increase in cell number and is thus a measure of cell proliferation. A dilution series of the test sample allows the calculation of the concentration resulting in 50% inhibition of cell proliferation ($IC_{50}$). The inhibitory capacity of the test sample may be compared to rapamycin and expressed as a relative $IC_{50}$ (i.e. test sample/$IC_{50}$ rapamycin). The compounds of Examples 1 and 2 have been found to have in this test a relative $IC_{50}$ of 0.2 and 0.09, respectively.

3. Macrophilin binding assay (MBA)

Rapamycin and the structurally related immunosuppressant, FK-506, are both known to bind in vivo to macrophilin-12 (also known as FK-506 binding protein or FKBP-12), and this binding is thought to be related to the immunosuppressive activity of these compounds. The Compounds of formula I also bind strongly to macrophilin-12, as is demonstrated in a competitive binding assay. In this assay, FK-506 coupled to BSA is used to coat microtiter wells. Biotinylated recombinant human macrophilin-12 (biot-MAP) is allowed to bind in the presence or absence of a test sample to the immobilized FK-506. After washing (to remove non-specifically bound macrophilin), bound biot-MAP is assessed by incubation with a streptavidin-alkaline phosphatase conjugate, followed by washing and subsequent addition of p-nitrophenyl phosphate as a substrate. The read-out is the OD at 405 nm. Binding of a test sample to biot-MAP results in a decrease in the amount of biot-MAP bound to the FK-506 and thus in a decrease in the OD405. A dilution series of the test sample allows determination of the concentration resulting in 50% inhibition of the biot-MAP binding to the immobilized FK-506 ($IC_{50}$). The inhibitory capacity of a test sample is compared to the $IC_{50}$ of free FK506 as a standard and expressed as a relative $IC_{50}$ (i.e., $IC_{50}$ test sample/$IC_{50}$-free FK506). In this assay, the compounds of Examples 1, 2 and 5 have been found to have a relative $IC_{50}$ of 1, 2.8 and 25, respectively.

4. Localized Graft-Versus-Host (GvH) Reaction

In vivo efficacy of the Compounds of formula I is proved in a suitable animal model, as described, e.g., in Ford et al, TRANSPLANTATION 10 (1970) 258. Spleen cells ($1 \times 10^7$) from 6 week old female Wistar/Furth (WF) rats are injected subcutaneously on day 0 into the left hind-paw of female (F344×WF)$F_1$ rats weighing about 100 g. Animals are treated for 4 consecutive days and the popliteal lymph nodes are removed and weighed on day 7. The difference in weight between the two lymph nodes is taken as the parameter for evaluating the reaction.

5. Kidney Allograt Reaction in Rat

One kidney from a DA($RT1^a$) or Brown-Norway (BN) ($RT1^n$) donor rat is transplanted onto the renal vessel of a unilaterally (left side) nephrectomized (Lewis $RT1^l$) recipient rat using an end-to-end anastomosis. Ureteric anastomosis is also end-to-end. Treatment commences on the day of transplantation and is continued for 14 days. A contralateral nephrectomy is done seven days after transplantation, leaving the recipient relying on the performance of the donor kidney. Survival of the graft recipient is taken as the parameter for a functional graft.

6. Experimentally Induced Allergic Encephalomyelitis (EAE) in Rats

Efficacy of the Compounds of formula I in EAE is measured, e.g., by the procedure described in Levine & Wenk, AMER J PATH 47 (1965) 61; McFarlin et al, J IMMUNOL 113 (1974) 712; Borel, TRANSPLANT. & CLIN. IMMUNOL 1 (1981) 3. EAE is a widely accepted model for multiple sclerosis. Male Wistar rats are injected in the hind paws with a mixture of bovine spinal cord and complete Freund's adjuvant. Symptoms of the disease (paralysis of the tail and both hind legs) usually develop within 16 days. The number of diseased animals as well as the time of onset of the disease are recorded.

7. Freund's Adjuvant Arthritis

Efficacy against experimentally induced arthritis is shown using the procedure described, e.g., in Winter & Nuss, ARTHRITIS & RHEUMATISM 9 (1966) 394; Billingham & Davies, HANDBOOK OF EXPERIMENTAL PHARMACOL (Vane & Ferreira Eds, Springer-Verlag, Berlin) 50/II (1979) 108–144. OFA and Wistar rats (male or female, 150 g body weight) are injected i.c. at the base of the tail or in the hind paw with 0.1 ml of mineral oil containing 0.6 mg of lyophilized heat-killed Mycobacterium smegmatis. In the developing arthritis model, treatment is started immediately after the injection of the adjuvant (days 1–18); in the established arthritis model treatment is started on day 14, when the secondary inflammation is well developed (days 14–20). At the end of the experiment, the swelling of the joints is measured by means of a micro-caliper. ED50 is the oral dose in mg/kg which reduces the swelling (primary or secondary) to half of that of the controls.

8. Antitumor and MDR activity

The antitumor activity of the compounds of formula I and their ability to enhance the performance of antitumor agents by alleviating multidrug resistance is demonstrated, e.g., by administration of an anticancer agent, e.g., colchicine or etoposide, to multidrug resistant cells and drug sensitive cells in vitro or to animals having multidrug resistant or drug sensitive tumors or infections, with and without co-administration of the compounds of formula I to be tested, and by administration of the compound of formula I alone.

Such in vitro testing is performed employing any appropriate drug resistant cell line and control (parental) cell line, generated, e.g. as described by Ling et al., J. Cell. Physiol. A, 103–116 (1974) and Bech-Hansen et al. J. Cell. Physiol. 88, 23–32 (1976). Particular clones chosen are the multidrug resistant (e.g. colchicine resistant) line CHR (subclone C5S3.2) and the parental, sensitive line AUX Bl (subclone ABl S11).

In vivo anti-tumor and anti-MDR activity is shown, e.g., in mice injected with multidrug resistant and drug sensitive cancer cells. Ehrlich ascites carcinoma (EA) sub-lines resistant to drug substance DR, VC, AK Er, TE or CC are developed by sequential transfer of EA cells to subsequent generations of BALB/c host mice in accordance with the methods described by Slater et al., J. Clin. Invest, 70, 1131 (1982).

Equivalent results may be obtained employing the compounds of formula I in test models of comparable design, e.g. in vitro, or employing test animals infected with drug-resistant and drug sensitive viral strains, antibiotic (e.g. penicillin) resistant and sensitive bacterial strains, anti-mycotic resistant and sensitive fungal strains as well as drug resistant protozoal strains, e.g. Plasmodial strains, for example naturally occurring sub-strains of *Plasmodium falciparum* exhibiting acquired chemotherapeutic, anti-malarial drug resistance.

9. Mip and Mip-like factor inhibition

Additionally, the compounds of formula I bind to and block a variety of Mip (macrophage infectivity potentiator) and Miplike factors, which are structurally similar to macrophilin. Mip and Mip-like factors are virulence factors produced by a wide variety of pathogens, including those of the genera Chlamidia e.g., *Chlamidia trachomatis;* Neisseria, e.g., *Neisseria meningitidis;* and Teginall e.g., *Legionella pneumophilia;* and also by the obligately parasitic members of the order Rickettsiales. These factors play a critical role in the establishment of intracellular infection. The efficacy of the compounds of formula I in reducing the infectivity of pathogens which produce Mip or Mip-like factors can be shown by comparing infectivity of the pathogens in cells culture in the presence and absence of the macrolides, e.g., using the methods described in Lundemose, et al., *Mol. Microbiol.* (1993) 7: 777.

10. Chronic Allogaft Rejection

The kidney of a male DA ($RT1^a$) rat is orthotopically transplanted into a male Lewis ($RT1^l$) recipient. In total 24 animals are transplanted. All animals are treated with cyclosporine A at 7.5 mg/kg/day per os for 14 days starting on the day of transplantation, to prevent acute cellular rejection. Contralateral nephrectomy is not performed. Each experimental group treated with a distinct dose of a compound of formula I or placebo comprises six animals.

Starting at day 53–64 after transplantation, the recipient animals are treated per os for another 69–72 days with a compound of formula I or receive placebo. At 14 days after transplantation animals are subjected to graft assessment by magnetic resonance imaging (MRI) with perfusion measurement of the kidneys (with comparison of the grafted kidney and the own contralateral kidney). This is repeated at days 53–64 after transplantation and at the end of the experiment. The animals are then autopsied. Rejection parameters such as MRI score, relative perfusion rate of the grafted kidney and histologic score of the kidney allograft for cellular rejection and vessel changes are determined and statistically analyzed. Administration of a compound of formula I, e.g. the compound of Example 1 or 2, at a dose of 0.5 to 2.5 mg/kg in this rat kidney allograft model yields a reduction in all above mentioned rejection parameters.

11. Angioplasty

Balloon catheterization is performed on day 0, essentially as described by Powell et al. (1989). Under Isofluorane anaesthesia, a Fogarty 2F catheter is introduced into the left common carotid artery via the external carotid and inflated (distension=10 $\mu$l $H_2O$). The inflated balloon is withdrawn along the length of the common carotid three times, the latter two times whilst twisting gently to obtain a uniform de-endothelialization. The cathether is then removed, a ligature placed around the external carotid to prevent bleeding and the animals allowed to recover.

2 groups of 12 RoRo rats (400 g, approximately 24 weeks old) are used for the study: one control group and one group receiving the compound to be tested. The rats are fully randomized during all handling, experimental procedures and analysis.

The compound to be tested is administered p.o. (gavage) starting 3 days before balloon injury (day −3) until the end of the study, 14 days after balloon injury (day +14). Rats are kept in individual cages and allowed food and water ad libitum.

The rats are then anaesthetized with Isofluorane, a perfusion catheter inserted through the left ventricle and secured in the aortic arch, and an aspiration cannula inserted into the right ventricle. Animals are perfused under a perfusion pressure of 150 mmHg, firstly for 1 min. with 0.1 M phosphate buffered saline solution (PBS, pH 7.4) and then for 15 min. with 2.5% glutaraldehyde in phosphate buffer (pH 7.4). The perfusion pressure is 150 mmHg at the tip of the cannula (=100 mmHg in the carotid artery, as determined in a preliminary experiment by introducing a cannula attached to a pressure transducer into the external carotid). Carotid arteries pre then excised, separated from surrounding tissue and immersed in 0.1 M cacodylate buffer (pH 7.4) containing 7% saccharose and incubated overnight at 4° C. The following day the carotids are immersed and shaken for 1 h at room temperature in 0.05% $KMnO_4$ in 0.1 M cacodylate. The tissues are then dehydrated in a graded ethanol series; 2×10 min in 75 %, 2×10 min in 85 %, 3×10 min in 95% and 3×10 min in 100% ethanol. The dehydrated carotids are then embedded in Technovit 7100 according to the manufacturers recommendation. The embedding medium is left to polymerize overnight in an exsiccator under argon, since oxygen is found to inhibit proper hardening of the blocks.

Sections 1–2 $\mu$m thick are cut from the middle section of each carotid with a hard metal knife on a rotary microtome and stained for 2 min with Giemse-stain. About 5 sections from each carotid are thus prepared and the cross-sectional areal of the media, neointima and the lumen morphometrically evaluated by means of an image analysis system (MCID, Toronto, Canada). In this assay, the compounds of formula I, e.g. the compound of Example 1 or 2, inhibit myointimal proliferation when administered per os at a daily dose of from 0.5 to 2.5 mg/kg.

The compounds of formula I are also useful in assays to detect the presence or amount of macrophilin-binding compounds, e.g., in competitive assays for diagnostic or screening purposes. Thus, in another embodiment, the invention provides for use of the compounds of formula I as a screening tool to determine the presence of macrophilin-binding compounds in a test solution, e.g., blood, blood serum, or test broth to be screened. Preferably, a compound of formula I is immobilized in microtiter wells and then allowed to bind in the presence and absence of a test solution to labelled macrophilin-12 (FKBP-12). Alternatively, the FKBP-12 immobilized in microtiter wells and allowed to bind in the presence and absence of a test solution to a compound of formula I which has been labelled, e.g., fluoro-, enzymatically- or radio-labelled, e.g., a compound of Formula I wherein $R_1$ comprises a labelling group. The plates are washed and the amount of bound labelled compound is measured. The amount of macrophilin-binding substance in the test solution is roughly inversely proportional to the amount of bound labelled compound. For quantitative analysis, a standard binding curve is made using known concentrations of macrophilin binding compound.

The Compounds of formula I are therefore useful in the following conditions:

a) Treatment and prevention of acute or chronic organ or tissue transplant rejection, e.g. for the treatment of recipients of e.g. heart, lung, combined heart-lung, liver, kidney, pancreatic, skin or corneal transplants. They are also indicated for the prevention of graft-versus-host disease, such as following bone marrow transplantation.

b) Treatment and prevention of transplant vasculopathies, e.g. atherosclerosis.

c) Treatment and prevention of smooth muscle cell proliferation and migration leading to vessel intimal thickening, blood vessel obstruction, obstructive coronary atherosclerosis, restenosis.

d) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of formula I may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

e) Treatment and prevention of asthma.

f) Treatment of multi-drug resistance (MDR). The compounds of formula I suppress P-glycoproteins (Pgp), which are the membrane transport molecules associated with MDR. MDR is particularly problematic in cancer patients and AIDS patients who will not respond to conventional chemotherapy because the medication is pumped out of the cells by Pgp. The compounds of formula I are therefore useful for enhancing the efficacy of other chemotherapeutic agents in the treatment and control of multidrug resistant conditions such as multidrug resistant cancer or multidrug resistant AIDS.

g) Treatment of proliferative disorders, e.g. tumors, hyperproliferative skin disorder and the like.

h) Treatment of fungal infections.

i) Treatment and prevention of inflammation, especially in potentiating the action of steroids.

j) Treatment and prevention of infection, especially infection by pathogens having Mip or Mip-like factors.

For the above indications the required dosage will of course vary, e.g. depending on the condition to be treated (for example the disease type or the nature of resistance), the effect desired and the mode of administration. In general however satisfactory results are obtained on administration orally at dosages on the order of from 0.05 to 5 or up to 10 mg/kg/day, e.g. on the order of from 0.1 to 2 or up to 7.5 mg/g/day administered once or, in divided doses 2 to 4× per day, or on administration parenterally, e.g. intravenously, for example by i.v. drip or infusion, at dosages on the order of from 0.01 to 2.5 up to 5 mg/kg/day, e.g. on the order of from 0.05 or 0.1 up to 1.0 mg/kg/day. Suitable daily dosages for patients are thus on the order of 500 mg p.o., e.g. on the order of from 5 to 100 mg p.o., or on the order of from 0.5 to 125 up to 250 mg i.v., e.g. on the order of from 2.5 to 50 mg i.v.

Alternatively and even preferably, dosaging is arranged in patient specific manner to provide pre-determined trough blood levels, e.g. as determined by RIA technique. Thus patient dosaging may be adjusted so as to achieve regular on-going trough blood levels as measured by RIA on the order of from 50 or 150 up to 500 or 1000 ng/ml, i.e. analogously to methods of dosaging currently employed for Ciclosporin immunosuppressive therapy.

The compounds of formula I may be administered as the sole active ingredient or together with other drugs. For example, in inmmunosuppressive applications such as prevention and treatment of graft vs. host disease, transplant rejection, or autoimmune disease, the compounds of formula I may be used in combination with cyclosporins or ascomycins, or their immunosuppressive analogs, e.g., cyclosporin A, cyclosporin G, FK-506, etc.; corticosteroids; cyclophosphamide; azathioprine; methotrexate; brequinar, leflunomide; mizoribine; mycophenolic acid; mycophenolate mofetil; immunosuppressive monoclonal antibodies, e.g., monoclonal antibodies to leukocyte receptors, e.g., MHC, CD2, CD3, CD4, CD7, CD25, CD28, CTLA4, B7, CD45, or CD58 or their ligands; or other immunomodulatory compounds. For anti-inflammatory applications, the compounds of formula I can be used together with anti-inflammatory agents, e.g., corticosteroids. For anti-infective applications, the compounds of formula I can be used in combination with other anti-infective agents, e.g., anti-viral drugs or antibiotics.

The compounds of formula I are administered by any conventional route, in particular enterally, e.g. orally, for example in the form of solutions for drinking, tablets or capsules or parenterally, for example in the form of injectable solutions or suspensions. Suitable unit dosage forms for oral administration comprise, e.g. from 1 to 50 mg of a compound of formula I, usually 1 to 10 mg. Pharmaceutical compositions comprising the compounds of formula I may be manufactured in conventional manner, e.g. analogously to pharmaceutical compositions comprising rapamycin, e.g., as described in EPA 0 041 795.

Preferably the pharmaceutical compositions comprise a compound of formula I and a carrier medium which medium comprises a hydrophilic phase, a lipophilic phase and a surfactant. They may be in the form of an emulsion or a microemulsion preconcentrate. Such emulsions or microemulsion preconcentrates are disclosed e.g. in UK Patent Application 2 278 780 A. Preferably, the lipophilic phase comprises 10 to 85% by weight of the carrier medium; the surfactant comprises 5 to 80% by weight of the carrier medium; the hydrophilic phase comprises 10 to 50% by weight of the carrier medium. The compound of formula I is preferably present in an amount of 2 to 15% by weight.

A particularly preferred pharmaceutical composition comprises a microemulsion preconcentrate carrier medium which comprises i) a reaction product of a castor oil and ethylene oxide, ii) a transesterification product of a vegetable oil and glycerol comprising predominantly linoleic acid or oleic acid, mono-, di- and triglycerides or a polyoxyalkylated vegetable oil, iii) 1,2-propylene glycol, and iv) ethanol.

In accordance with the foregoing the present invention also provides:

A. a compound of formula I for use as a pharmaceutical, for example in the prevention or treatment of above indicated disorders.

B. a pharmaceutical composition comprising a compound of formula I together with a pharmaceutically acceptable diluent or carrier therefor.

C. a method of preventing or treating disorders as indicated above in a subject in need of such treatment, which method comprises administering to said subject an effective amount of a compound of formula I.

D. a kit or package for use in immunosuppression, inflammation or infections as indicated above, including a pharmaceutical composition comprising a compound of formula I and a pharmaceutical composition comprising either an immunosuppressant or immunomodulatory drug or an anti-inflammatory agent or an anti-infective agent.

It has also surprisingly been found that the compounds of formula I wherein X is OH i.e. 32(S)-dihydro compounds have an improved activity, e.g. in the above disclosed assays, and are more stable than the corresponding enantiomers, i.e. the 32(R)dihydro compounds, e.g. when submitted to the following test:

The compounds to be tested are incubated in rat serum and their binding affinity for FKBP12 is measured in the MBA assay after different incubation times. As the affinity decreases the nominal IC50 increases. A decrease in affinity is generally attributed to instability of the compound in rat serum.

What is claimed is:

1. A method for preventing or treating acute or chronic organ or tissue transplant rejection, or transplant vasculopathies in a subject in need of such treatment, which comprises administering to said subject an effective amount of a compound of formula I

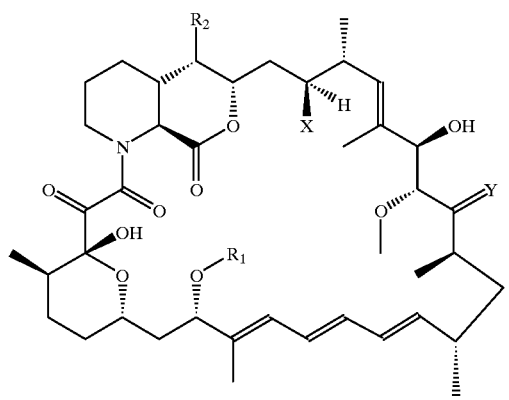

I wherein
  $R_1$ is alkyl, alkenyl, alkynyl, hydroxyalkyl, hydroxyalkenyl, hydroxyalkynyl, benzyl, alkoxybenzyl, or chlorobenzyl;
  $R_2$ is selected from formula II or formula III:

Formula II

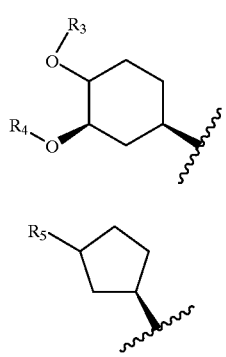

Formula III wherein
  $R_3$ is H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl, or alkylsilyl;

$R_4$ is H, methyl or together with $R_3$ forms $C_{2-6}$ alkylene;

$R_5$ is $R_6O$—$CH_2$—, wherein $R_6$ is H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxy-carbonylaminoalkyl, alkylcarbonylaminoalkyl, arylsulfonamidoalkyl, allyl, dihydroxyalkylallyl, dioxolanylallyl, or carbalkoxyalkyl;

$R_7CO$—, wherein $R_7$ is H, alkyl, hydroxy, alkoxy, aryloxy, amino, alkylamino, or N,N-disubstituted-amino wherein the substituents are alkyl, aryl, or arylalkyl;

$R_8NCH$—, wherein $R_8$ is alkyl, aryl, amino, alkylamino, arylamino, hydroxy, alkoxy, or arylsulfonylamino; or

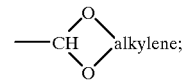

Y is O, (H, OH), or (H, $C_{1-4}$alkoxy); and
X is OH or H;
wherein "alk" or "alkyl" refers to a $C_{1-10}$ aliphatic substituent optionally interrupted by an oxy linkage; and "ar" or "aryl" refers phenyl, benzyl, tolyl, and pyridyl, provided that, when X is OH, $R_1$ is alkyl and $R_2$ is a residue of formula 11, then $R_3$ is other than H.

2. A method of claim 1, wherein the compound is of formula Ia

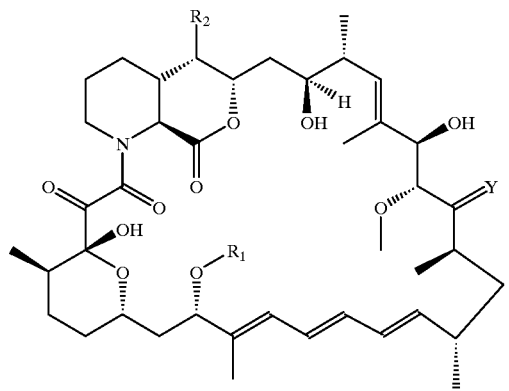

Ia wherein
  $R_1$ is $C_{3-10}$alk-2-ynyl or $C_{3-10}$hydroxyalk-2-ynyl;

$R_2$ is selected from formula II or formula III:

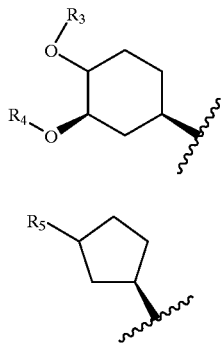

Formula II

Formula III wherein $R_3$ is H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl, or alkylsilyl;

$R_4$ is H, methyl, or together with $R_3$ forms $C_{2-6}$ alkylene;

$R_5$ is $R_6O-CH_2-$, wherein $R_6$ is H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, or carbalkoxyalkyl;

$R_7CO-$, wherein $R_7$ is H, alkyl, hydroxy, alkoxy, aryloxy, amino, alkylamino, or N,N-disubstituted-amino wherein the substituents are alkyl, aryl, or arylalkyl;

$R_8NCH-$, wherein $R_8$ is alkyl, aryl, amino, alkylamino, arylamino, hydroxy, alkoxy or arylsulfonylamino; or

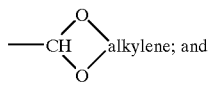 alkylene; and

Y is O;

wherein "alk" or "alkyl" refers to a $C_{1-10}$ aliphatic substituent optionally interrupted by an oxy linkage; and "ar" or "aryl" refers to phenyl, benzyl, tolyl, and pyridyl.

3. A method of claim 1, wherein the compound is of formula Ib

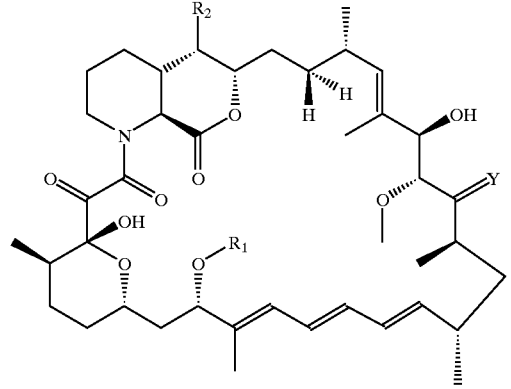

Ib wherein $R_1$ is $C_{1-10}$alkyl, $C_{3-10}$alkenyl, $C_{3-10}$hydroxyalkenyl, $C_{3-10}$alk-2-ynyl, $C_{3-10}$hydroxyalk-2-ynyl, or $C_{1-10}$alkoxy $C_{1-10}$alkyl;

$R_2$ is selected from formula II or formula III:

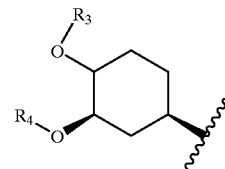

Formula II

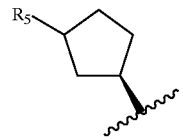

Formula III wherein $R_3$ is H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl, or alkylsilyl;

$R_4$ is H, methyl or together with $R_3$ forms $C_{2-6}$alkylene;

$R_5$ is $R_6O-CH_2-$, wherein $R_6$ is H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, or carbalkoxyalkyl;

$R_7CO-$, wherein $R_7$ is H, alkyl, hydroxy, alkoxy, aryloxy, amino, alkylamino, or N,N-disubstituted-amino wherein the substituents are alkyl, aryl, or arylalkyl;

R₈NCH—, wherein R₈ is alkyl, aryl, amino, alkylamino, arylamino, hydroxy, alkoxy, or arylsulfonylamino; or

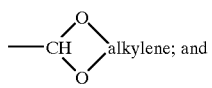

Y is O;

wherein "alk" or "alkyl" refers to a C₁₋₁₀ aliphatic substituent optionally interrupted by an oxy linkage; and "ar" or "aryl" refers to phenyl, benzyl, tolyl, and pyridyl.

4. A method of claim 1, wherein the compound is 16-pent-2-ynyloxy-32(S)-dihydro-rapamycin or 16-pent-2-ynyloxy-32(S)-dihydro-40-O-(2-hydroxyethyl)-rapamycin.

5. A method of claim 1, wherein the compound is 32-deoxo-rapamycin or 16-pent-2-ynyloxy-32-deoxo-rapamycin.

6. A method of claim 1 for preventing acute or chronic organ or tissue transplant rejection, wherein the compound is 16-pent-2-ynyloxy-32(S)-dihydro-rapamycin or 16-pent-2-ynyloxy-32(S)-dihydro-40-O-(2-hydroxyethyl)-rapamycin.

7. A method of claim 1 for preventing acute or chronic organ or tissue transplant rejection, wherein the compound is 32-deoxo-rapamycin or 16-pent-2-ynyloxy-32-deoxo-rapamycin.

8. A method of claim 1 for treating acute or chronic organ or tissue transplant rejection, wherein the compound is 16-pent-2-ynyloxy-32(S)-dihydro-rapamycin or 16-pent-2-ynyloxy-32(S)-dihydro-40-O-(2-hydroxyethyl)-rapamycin.

9. A method of claim 1 for treating acute or chronic organ or tissue transplant rejection, wherein the compound is 32-deoxo-rapamycin or 16-pent-2-ynyloxy-32-deoxo-rapamycin.

10. A method of claim 1 for preventing transplant vasculopathies, wherein the compound is 16-pent-2-ynyloxy-32(S)-dihydrorapamycin or 16-pent-2-ynyloxy-32(S)-dihydro-40-O-(2-hydroxyethyl)-rapamycin.

11. A method of claim 1 for preventing transplant vasculopathies, wherein the compound is 32-deoxo-rapamycin or 16-pent-2-ynyloxy-32-deoxo-rapamycin.

12. A method of claim 1 for treating transplant vasculopathies, wherein the compound is 16-pent-2-ynyloxy-32(S)-dihydro-rapamycin or 16-pent-2-ynyloxy-32(S)-dihydro-40-O-(2-hydroxyethyl)-rapamycin.

13. A method of claim 1 for treating transplant vasculopathies, wherein the compound is 32-deoxo-rapamycin or 16-pent-2-ynyloxy-32-deoxo-rapamycin.

14. A method for treating smooth muscle cell proliferation and migration leading to vessel intimal thickening in a subject in need of such treatment, which comprises administering to said subject an effective amount of a compound of formula I

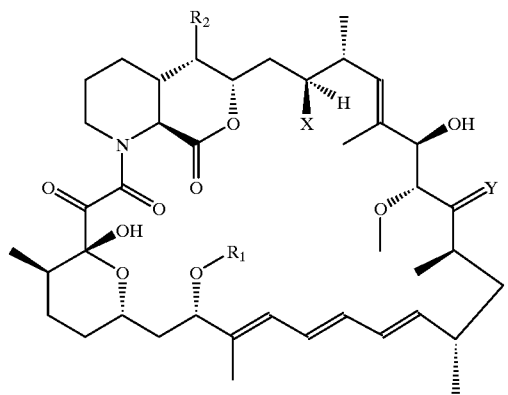

wherein
R₁ is alkyl, alkenyl, alkynyl, hydroxyalkyl, hydroxyalkenyl, hydroxyalkynyl, benzyl, alkoxybenzyl, or chlorobenzyl;
R₂ is selected from formula II or formula III:

Formula II

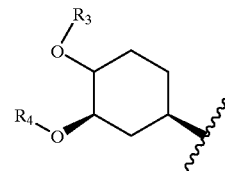

Formula III

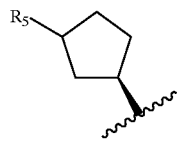

wherein
R₃ is H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl, or alkylsilyl;
R₄ is H, methyl or together with R₃ forms C₂₋₆alkylene;
R₅ is R₆O—H₂—, wherein R₅ is H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylakyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxy-carbonylaminoalkyl, alkylcarbonylaminoalkyl, arylsulfonamidoalkyl, allyl, dihydroxyalkylallyl, dioxolanylallyl, or carbalkoxyalkyl;

$R_7CO$—, wherein $R_7$ is H, allyl, hydroxy, alkoxy, aryloxy, amino, alkylamino, or N,N-disubstituted-amino wherein the substituents are alkyl, aryl, or arylalkyl;

$R_8NCH$—, wherein $R_8$ is alkyl, aryl, amino, alkylamino, arylamino, hydroxy, alkoxy, or arylsulfonylamino; or

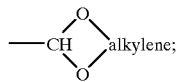

Y is O, (H, )H), or (H, $C_{1-4}$alkoxy); and

X is OH or H;

wherein "alk" or "alkyl" refers to a $C_{1-10}$aliphatic substituent optionally interrupted by an oxy linkage; and "arm or "aryl" refers phenyl, benzyl, tolyl, and pyridyl, provided that, when X is OH, $R_1$ is alkyl and $R_2$ is a residue of formula II, then $R_3$ is other than H.

15. A method of claim 14, wherein the compound is of formula Ia

Ia

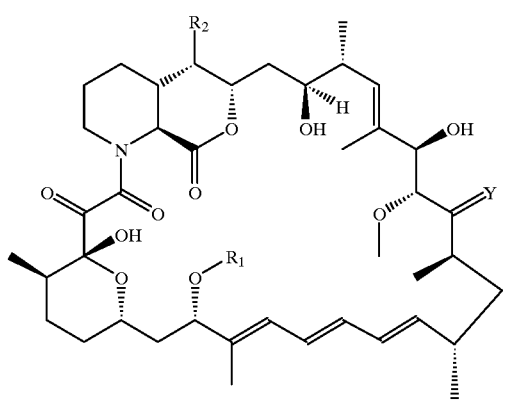

wherein $R_1$ is $C_{1-10}$alk-2-ynyl or $C_{3-10}$hydroxyalk-2-ynyl;

$R_2$ is selected from formula II or formula III:

Formula II

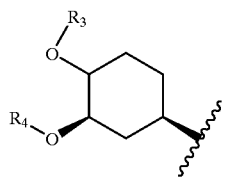

Formula III

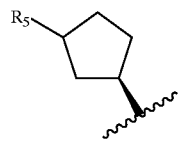

wherein $R_3$ is H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl, or alkylsilyl;

$R_4$ is H, methyl, or together with $R_3$ forms $C_{2-8}$alkylene;

$R_5$ is $R_6O$—$OH_2$—, wherein $R_5$ is H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfamidoalkyl, allyl, dihydroxyalkylallyl, dioxolanylallyl, or carbalkoxyalkyl;

$R_7CO$—, wherein $R_7$ is H, alkyl, hydroxy, alkoxy, aryloxy, amino, alkylamino, or N,N-disubstituted-amino wherein the substituents are alkyl, aryl, or arylalkyl;

$R_8NCH$—, wherein $R_8$ is alkyl, aryl, amino, alkylamino, arylamino, hydroxy, alkoxy or arylsulfonylamino; or

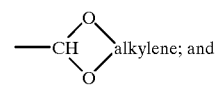

Y is O;

wherein "alk" or "alkyl" refers to a $C_{1-10}$aliphatic substituent optionally interrupted by an oxy linkage; and "ar" or "aryl" refers to phenyl, benzyl, tolyl, and pyridyl.

16. A method of claim 14, wherein the compound is of formula Ib

Ib

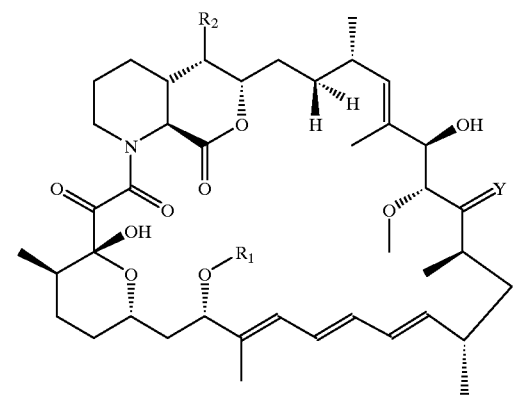

wherein $R_1$ is $C_{1-10}$alkyl, $C_{3-10}$hydroxyalkenyl, $C_{3-10}$hydroxyalkenyl, $C_{3-10}$alk-2-ynyl, $C_{3-10}$hydroxyalk-2-ynyl, or $C_{1-10}$alkoxy $C_{1-10}$alkyl;

$R_2$ is selected from formula II or formula III:

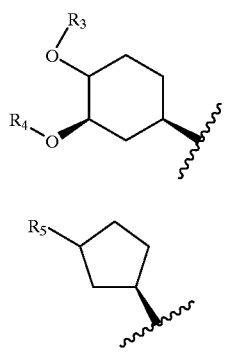

Formula II

Formula III wherein
- $R_3$ is H, alkyl, alkenyl, alkynyl, aryl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoallyl, alkylaminoalkyl, alkoxycarbonylaminoalkyl, alkylcarbonylaminoalkyl, arylsulfonamidoalkyl, allyl, dihydroxyalkylallyl, dioxolanylallyl, carbalkoxyalkyl, or alkylsilyl;
- $R_4$ is H, methyl or together with $R_3$ forms $C_{2-6}$alkylene;
- $R_5$ is $R_5O$—$CH_2$—, wherein $R_5$ is H, alkyl, alkenyl, alkynyl, aryl, alkylcarbonyl, arylcarbonyl, heteroarylcarbonyl, hydroxyalkylcarbonyl, aminoalkylcarbonyl, formyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, alkylcarbonyloxyalkyl, aminoalkyl, alkylaminoalkyl, alkoxycarbonylaminoalkyl, alkylcarbonylaminoalkyl, arylsulfonamidoalkyl, allyl, dihydroxyalkylallyl dioxolanylallyl, or carbalkoxyalkyl;
- $R_7CO$—, wherein $R_7$ is H, alkyl, hydroxy, alkoxy, aryloxy, amino, alkylamino, or N,N-disubstituted-amino wherein the substituents are alkyl, aryl, or arylalkyl;
- $R_8NCH$—, wherein $R_8$ is alkyl, aryl, amino, alkylamino, arylamino, hydroxy, alkoxy, or arylsulfonylamino; or

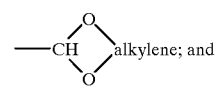 alkylene; and

Y is O;

wherein "alk" or "alkyl" refers to a $C_{1-10}$ aliphatic substituent optionally interrupted by an oxy linkage; and "ar" or "aryl" refers to phenyl, benzyl, tolyl, and pyridyl.

17. A method of claim 14, wherein the compound is 16-pent-2-ynyloxy-32(S)-dihydro-rapamycin or 16-pent-2-ynyloxy-32(S)dihydro -40-O-(2-hydroxyethyl)-rapamycin.

18. A method of claim 14, wherein the compound is 32-deoxo-rapamycin or 16-pent-2-ynyloxy-32-deoxo-rapamycin.

* * * * *

UNITED STATES PATENT AND TRADEMARK OFFICE
CERTIFICATE OF CORRECTION

PATENT NO. : 6,200,985 B1
DATED : March 13, 2001
INVENTOR(S) : Cottens et al.

Page 1 of 2

It is certified that error appears in the above-identified patent and that said Letters Patent is hereby corrected as shown below:

Title page,
Left column, setion [30] Foreign Application Priority Data should read:

-- [30] Foreign Application Priority Data
Jun. 9, 1995 (GB) .....................9511704
July 6, 1995 (GB).....................9513754 --.

Column 23,
Line 44, should read: -- ynyloxy-32(S)-dihydro-rapamycin or 16-pent-2-ynyloxy-32 --.

Column 24,
Line 52, should read: -- $R_5$ is $R_6O\text{-}CH_2\text{-}$, wherein $R_5$ is H, alkyl, alkenyl, --.

Column 25,
Line 1, should read: -- $R_7CO\text{-}$, wherein $R_7$ is H, alkyl, hydroxy, alkoxy, aryloxy, --.
Line 12, should read: -- Y is O, (H, OH), or (H, $C_{1-4}$alkoxy); and --.
Line 16, should read: -- "ar" or "aryl" refers phenyl, benzyl, tolyl, and pyridyl, --.
Line 41, should read: -- R1 is $C_{3-10}$alk-2-ynyl or $C_{3-10}$hydroxyalk-2-ynyl; --.

Column 26,
Lines 6 and 7, should read: -- $R_4$ is H, methyl, or together with $R_3$ forms $C_{2-6}$alkylene; $R_5$ is $R_6O\text{-}CH_2\text{-}$, wherein $R_6$ is H, alkyl, alkenyl, --.
Line 18, should read: -- alkylcarbonylaminoalkyl, arylsulfonamidoalkyl, allyl, --.
Line 62, should read: -- $R_1$ is $C_{1-10}$alkyl, $C_{3-10}$alkenyl, --.

Column 27,
Line 23, should read: -- alkoxyalkyl, alkylcarbonyloxyalkyl, aminoalkyl, --.
Line 29, should read: -- $R_5$ is $R_6O\text{-}CH_2\text{-}$, wherein $R_6$ is H, alkyl, alkenyl, --.

UNITED STATES PATENT AND TRADEMARK OFFICE
CERTIFICATE OF CORRECTION

PATENT NO. : 6,200,985 B1
DATED : March 13, 2001
INVENTOR(S) : Cottens et al.

It is certified that error appears in the above-identified patent and that said Letters Patent is hereby corrected as shown below:

Column 28,
Line 28, should read: -- ynyloxy-32(S)-dihydro-40-O-(2-hydroxyethyl)-rapamycin --.

Signed and Sealed this

Sixteenth Day of October, 2001

Attest:

NICHOLAS P. GODICI
*Attesting Officer*     *Acting Director of the United States Patent and Trademark Office*